US00PP34297P2

(12) United States Plant Patent
Wood

(10) Patent No.: US PP34,297 P2
(45) Date of Patent: Jun. 7, 2022

(54) ***WEIGELA* PLANT NAMED 'SMNWFBGV'**

(50) Latin Name: *Weigela florida*
Varietal Denomination: SMNWFBGV

(71) Applicant: Timothy D. Wood, Spring Lake, MI (US)

(72) Inventor: Timothy D. Wood, Spring Lake, MI (US)

(73) Assignee: SPRING MEADOW NURSERY INC., Grand Haven, MI (US)

( * ) Notice: Subject to any disclaimer, the term of this patent is extended or adjusted under 35 U.S.C. 154(b) by 0 days.

(21) Appl. No.: 17/492,640

(22) Filed: Oct. 3, 2021

(51) Int. Cl.
*A01H 5/02* (2018.01)
*A01H 6/00* (2018.01)

(52) U.S. Cl.
USPC ..... Plt./226
CPC ..... *A01H 6/00* (2018.05)

(58) Field of Classification Search
USPC ..... Plt./226
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Weigela* plant named 'SMNWFBGV', characterized by its relatively compact, upright to outwardly spreading and uniformly mounding plant habit; freely branching habit; dense and bushy appearance; variegated leaves with olive green-colored centers surrounded with dark reddish brown-colored margins; freely flowering habit; purplish red-colored flowers that do not fully open and remain in bud-like; and good garden performance.

2 Drawing Sheets

Figure 1:
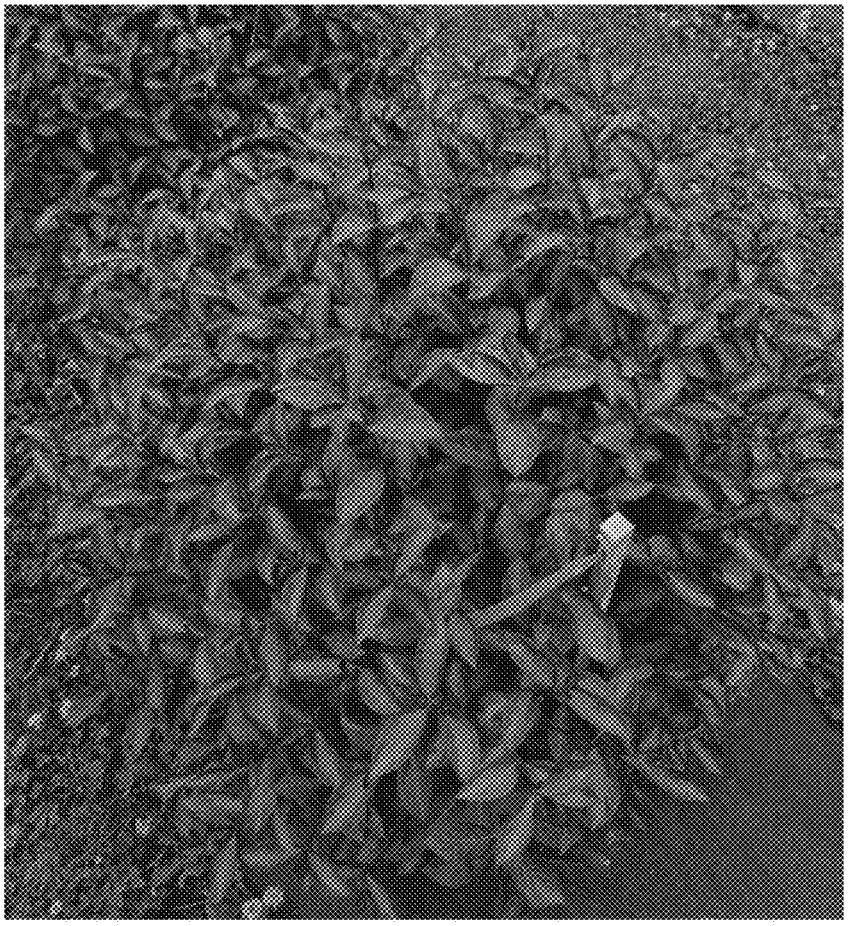

Botanical designation: *Weigela florida.*
Cultivar denomination: 'SMNWFBGV'.

STATEMENT REGARDING PRIOR DISCLOSURES BY INVENTOR/APPLICANT & ASSIGNEE

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Weigela* plant, botanically known as *Weigela florida* and hereinafter referred to by the name 'SMNWFBGV'.

The new *Weigela* plant is a product of a planned breeding program conducted by the Inventor in Grand Haven, Mich. The objective of the breeding program was to develop new compact and remontant-flowering *Weigela* plants with attractive flower colors.

The new *Weigela* plant is a naturally-occurring branch mutation of an unnamed proprietary seedling selection of *Weigela florida*, not patented. The new *Weigela* plant was discovered and selected by the Inventor on a single plant within a population of plants of the seedling selection in a controlled environment in Grand Haven, Mich. during the summer of 2013.

Asexual reproduction of the new *Weigela* plant by softwood stem cuttings since 2016 in Grand Haven, Mich. has shown that the unique features of this new *Weigela* plant are stable and reproduced true to type in successive generations of asexual reproduction.

SUMMARY OF THE INVENTION

Plants of the new *Weigela* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNWFBGV'. These characteristics in combination distinguish 'SMNWFBGV' as a new and distinct *Weigela* plant:

1. Relatively compact, upright to outwardly spreading and uniformly mounding plant habit.
2. Freely branching habit; dense and bushy appearance.
3. Variegated leaves with olive green-colored centers surrounded with dark reddish brown-colored margins.
4. Freely flowering habit.
5. Purplish red-colored flowers that do not fully open and remain bud-like.
6. Good garden performance.

In side-by-side comparisons conducted in Grand Haven, Mich., plants of the new *Weigela* differ primarily from plants of the mutation parent in leaf color as plants of the new *Weigela* have variegated leaves whereas plants of the mutation parent have non-variegated leaves.

Plants of the new *Weigela* can be compared to plants of the *Weigela florida* 'Kolmagira', disclosed in U.S. Plant Pat.

No. 20,384. In side-by-side comparisons plants of the new *Weigela* differ primarily from plants of 'Kolmagira' in the following characteristics:

1. Plants of the new *Weigela* have variegated leaves with olive green-colored centers surrounded with dark reddish brown-colored margins whereas plants of 'Kolmagira' have variegated leaves with yellow green and dark green-colored centers with purple-colored margins.
2. Plants of the new *Weigela* have flowers that do not fully open whereas plants of 'Kolmagira' have flowers which fully open.

Plants of the new *Weigela* can also be compared to plants of the *Weigela florida* 'SMNWFMS', disclosed in U.S. Plant Pat. No. 26,922. In side-by-side comparisons plants of the new *Weigela* differ primarily from plants of 'SMNWFMS' in the following characteristics:

1. Plants of the new *Weigela* have variegated leaves with olive green-colored centers surrounded with dark reddish brown-colored margins whereas plants of 'SMNWFMS' have non-variegated leaves that are dark burgundy to almost black in color.
2. Plants of the new *Weigela* have flowers that do not fully open whereas plants of 'SMNWFMS' have flowers which fully open.

BRIEF DESCRIPTION OF THE PHOTOGRAPHS

The accompanying colored photographs illustrate the overall appearance of the new *Weigela* plant showing the colors as true as it is reasonably possible to obtain in colored reproductions of this type. Colors in the photographs may differ slightly from the color values cited in the detailed botanical description which accurately describe the colors of the new *Weigela* plant.

The photograph on the first sheet (FIG. 1) is a side perspective view of a typical plant of 'SMNWFBGV' grown in a container.

Figure 2:
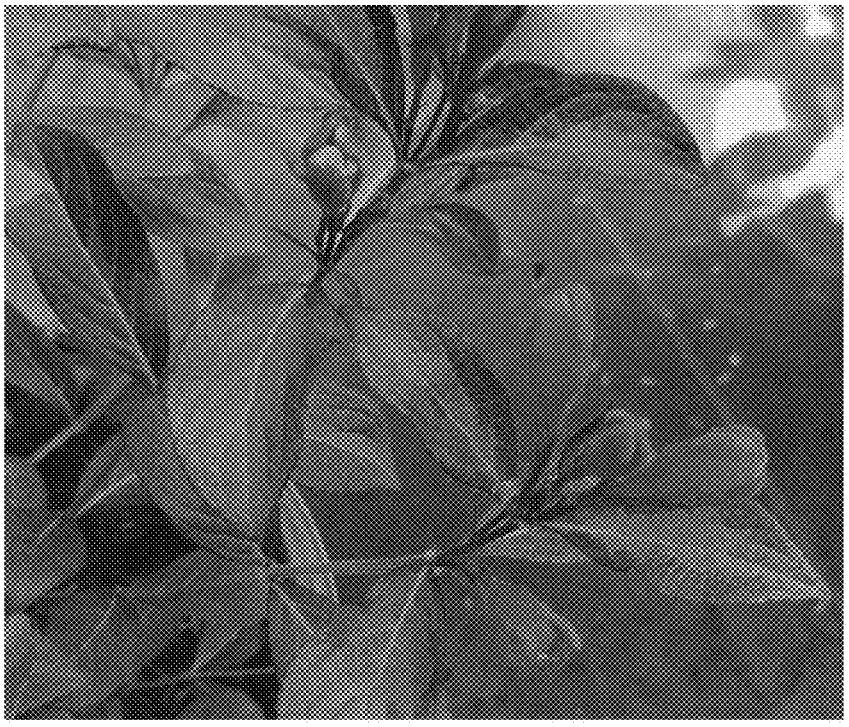

The photograph on the second sheet (FIG. 2) is a close-up view of a typical flowering branch of 'SMNWFBGV'.

DETAILED BOTANICAL DESCRIPTION

Plants used for the aforementioned photographs and the following description were grown during the spring and early summer in three-gallon containers in a polypropylene-covered greenhouse in Grand Haven, Mich. and under cultural practices typical of commercial *Weigela* production. During the production of the plants, day temperatures ranged from 18° C. to 27° C. and night temperatures ranged from 5° C. to 10° C. Plants of the new *Weigela* were two years old when the photographs and description were taken. In the following description, color references are made to The Royal Horticultural Society Colour Chart, 2015 Edition, except where general terms of ordinary dictionary significance are used.

Botanical classification: *Weigela florida* 'SMNWFBGV'.

Parentage: Naturally-occurring branch mutation of an unnamed proprietary seedling selection of *Weigela florida*, not patented.

Propagation:

*Type.*—By softwood stem cuttings.

*Time to initiate roots, summer.*—About 15 days at temperatures about 18° C. to 27° C.

*Time to produce a rooted young plant, summer.*—About two months at temperatures about 18° C. to 27° C.

*Root description.*—Fine; fibrous; typically white in color, actual color of the roots is dependent on substrate composition, water quality, fertilizer, substrate temperature and physiological age of roots.

*Rooting habit.*—Freely branching; dense.

Plant description:

*Plant and growth habit.*—Perennial shrub; relatively compact, upright to outwardly spreading and uniformly mounding plant habit; vigorous growth habit and rapid growth rate.

*Branching habit.*—Freely branching habit with about 15 to 20 lateral branches developing per plant; pinching enhances lateral branch development; dense and bushy plant form.

*Plant height.*—About 50 cm.

*Plant diameter.*—About 60 cm.

Lateral branch description:

*Length.*—About 45 cm.

*Diameter.*—About 4 mm.

*Internode length.*—About 5 cm.

*Texture.*—When developing, slightly pubescent along longitudinal ridges; with development becoming glabrous.

*Strength.*—Strong, somewhat flexible.

*Aspect.*—Upright to about 45° from vertical.

*Color, developing.*—Close to 144C; surfaces exposed to sunlight are tinged with close to 166A.

*Color, developed.*—Close to 199A to 199B.

Leaf description:

*Arrangement.*—Opposite; simple.

*Length.*—About 7 cm.

*Width.*—About 3.5 cm.

*Shape.*—Elliptical.

*Apex.*—Acuminate.

*Base.*—Cuneate.

*Margin.*—Entire to slightly serrulate.

*Texture, upper surface.*—Rough, glabrous; coriaceous.

*Texture, lower surface.*—Rough, pubescence along midvein; prominent venation; coriaceous.

*Venation pattern.*—Pinnate.

*Color.*—Developing and fully expanded leaves, upper surface: Centers, close to 146B surrounded with close to 200A; venation, close to 144C. Developing and fully expanded leaves, lower surface: Centers, close to 146D surrounded with close to 200B; venation, close to 144C.

*Petioles.*—Length: About 5 mm. Diameter: About 2 mm. Texture, upper and lower surfaces: Slightly pubescent. Color, upper and lower surfaces: Close to 144C and 200A.

Flower description:

*Flower arrangement and habit.*—Salverform flowers arranged in terminal clusters each with about two to three flowers; about 20 to 25 flowers develop per lateral stem during the flowering season; flowers do not fully open and remain in bud-like; flowers face mostly upright.

*Fragrance.*—None detected.

*Natural flowering season.*—Plants of the new *Weigela* flower during the late spring and early summer in Grand Haven, Mich.; flowers not persistent.

*Flower buds.*—Length: About 3 cm. Diameter: About 8 mm. Shape: Obovate to spatulate. Color: Close to 60A.

*Flower diameter.*—About 1 cm.

*Flower length* (*height*).—About 3.5 cm.

*Flower throat diameter.*—About 1 cm.

*Flower tube length.*—About 1 cm.

*Flower tube diameter, proximally.*—About 3 mm.

*Corolla.*—Arrangement: Salverform; five petals fused into a tube with separate petal lobes. Petal lobe length: About 8 mm. Petal lobe width: About 1 cm. Petal lobe shape: Rounded to obovate. Petal lobe apex: Obtuse. Petal lobe margin: Entire. Petal texture, upper and lower surfaces: Smooth, glabrous; silky. Throat and tube texture: Smooth, glabrous. Color: Developing and fully developed, upper surface: Close to 63A; venation, close to 63A. Developing and fully developed, lower surface: Close to 60A; venation, close to 60A. Throat: Close to 60A; venation, close to 60A. Tube: Close to 60A; venation, close to 60A.

*Sepals.*—Quantity per flower: Five in a single whorl, fused; campanulate calyx. Length: About 5 mm. Width: About 1 mm. Shape: Narrowly triangular, elongated. Apex: Acuminate. Base: Obtuse. Margin: Entire. Sepal texture, upper and lower surfaces: Smooth; glabrous; coriaceous. Color, upper and lower surfaces: Close to N186C.

*Peduncles.*—Length: About 1 cm. Diameter: About 1 mm. Strength: Strong; flexible. Aspect: Upright to about 15° from vertical. Texture: Smooth, glabrous. Color: Close to 144C.

*Reproductive organs.*—Stamens: Quantity and arrangement: Four or five per flower. Filament length: About 1.4 cm. Filament color: Close to NN155C. Anther shape: Narrowly oblong. Anther size: About 6 mm. Anther color: Close to 158A. Pollen amount: Abundant. Pollen color: Close to NN155A. Pistils: Quantity: One per flower. Pistil length: About 3.5 cm. Style length: About 3.25 cm. Style color: Close to NN155C. Stigma shape: Globular. Stigma color: Close to NN155A. Seeds and fruits: To date, seed and fruit development has not been observed on plants of the new *Weigela*.

Garden performance: Plants of the new *Weigela* have exhibited good garden performance.

Pathogen & pest resistance: To date, plants of the new *Weigela* have not been observed to be resistant to pathogens and pests common to *Weigela* plants.

It is claimed:

1. A new and distinct *Weigela* plant named 'SMNWFBGV' as illustrated and described.

* * * * *